United States Patent [19]

Brooks et al.

[11] Patent Number: 5,683,554
[45] Date of Patent: Nov. 4, 1997

[54] F141B CRUDE STABILIZATION

[75] Inventors: Wayne E. Brooks, Paducah; Craig Jolley, Calvert City, both of Ky.

[73] Assignee: Elf Atochem North America, Inc., Philadelphia, Pa.

[21] Appl. No.: 509,840

[22] Filed: Aug. 1, 1995

Related U.S. Application Data

[63] Continuation-in-part of Ser. No. 218,515, Mar. 25, 1994, abandoned.

[51] Int. Cl.$^6$ ............................ B01D 3/34; C07C 17/38
[52] U.S. Cl. .................. 203/6; 203/99; 203/DIG. 19; 203/2; 570/178
[58] Field of Search ........................ 203/6, 8, 2, 91, 203/99, DIG. 19, DIG. 18; 570/178, 177

[56] References Cited

U.S. PATENT DOCUMENTS

| | | | |
|---|---|---|---|
| 3,763,017 | 10/1973 | Yves et al. | 203/6 |
| 4,422,913 | 12/1983 | Larsen et al. | 570/123 |
| 4,948,479 | 8/1990 | Brooks et al. | 204/158.21 |
| 4,975,156 | 12/1990 | Wismer | 203/39 |
| 5,105,035 | 4/1992 | Wang et al. | 570/178 |
| 5,126,067 | 6/1992 | Swan et al. | 203/67 |
| 5,135,680 | 8/1992 | Crooker et al. | 252/350 |
| 5,169,995 | 12/1992 | Crooker et al. | 570/119 |
| 5,306,850 | 4/1994 | Darago | 570/178 |

FOREIGN PATENT DOCUMENTS

| | | | |
|---|---|---|---|
| 2689885 | 10/1993 | France . | |
| 0046804 | 12/1978 | Japan | 203/6 |

OTHER PUBLICATIONS

U.S. Patent Application, IR 3309A, "Inhibition of 141B Decomposition", *corresponds to 2689885, France.

*Primary Examiner*—Virginia Manoharan
*Attorney, Agent, or Firm*—Ratner & Prestia

[57] ABSTRACT

Separation of 1,1-dichloro-1-fluoroethane (141b) from lower boiling components contained in a crude 141b feed stream mixture by adding the feed stream mixture, and, based upon the weight of 141b in the feed stream mixture, between 100 and 300 ppm of a component that will inhibit formation of 1,1-difluoro-1-chloroethane into a feed line of a distillation column operated at between 3 and 165 psig pressure with a temperature between 100° F. and 250° F. in the bottom reboiler section of the column.

4 Claims, No Drawings

F141B CRUDE STABILIZATION

This application is a Continuation-In-Part of U.S. patent application Ser. No. 08/218,515 filed Mar. 25, 1994 now abandoned.

FIELD OF THE INVENTION

The present invention relates to a method of inhibiting the formation of unwanted by-products during the heating of 1,1-dichloro-1-fluoroethane ("141b"), especially as it relates to the separation of 141b from a liquid mixture containing halohydrocarbons having a lower boiling point than that of 141b, mainly 1,1-difluoro-1-chloroethane ("142b"), via distillation. More particularly, it relates to the prevention of recontamination of 141b in the bottoms of the distillation column with 142b due to possible decomposition of 141b in the bottoms.

BACKGROUND OF THE INVENTION

The hydrochlorofluorocarbon 141b is a replacement for trichlorofluoromethane ("11") as a foam blowing agent. As shown by Brooks et al. in U.S. Pat. No. 4,948,479 (the entire specification of which is hereby incorporated by reference), however, the manufacture of 141b from 1,1,1-trichloroethane ("140a") and hydrogen fluoride ("HF") results in the formation of vinylidene chloride ("1130a") and other unsaturated by-products and acids, principally HCl. Because of similar boiling points, 141b (b.p. 32° C.) and 1130a (b.p. 37° C.) cannot be readily separated by distillation. Thus, Brooks et al. teach the use of a photochlorination step to convert the 1130a in the 141b product stream to the higher boiling 1,1,1,2-tetrachloroethane ("130a") (b.p. 130.5° C.), then distillation of the photochlorinated liquid mixture to separate the low boiling 141b from the higher boiling liquids such as 130a (and possibly 1,1,1-trichloroethane ["140a"] unless it has been removed upstream). Brooks et al. further teach that it is first necessary to reduce the amount of 142b present in the crude 141b to no more than 100 parts per million, before photochlorination, in order to minimize the production of 1,2-dichloro-1,1-difluoroethane, a suspected carcinogen. This is a possible reaction product of 142b with excess chlorine during the photochlorination step, and one which is difficult to separate from 141b due to relative closeness in boiling points. Sometimes, however, the residual 142b in the 141b bottoms from the foregoing preliminary distillation step remains too high, of the order 140 to 600 parts per million. It has been postulated that this results from a breakdown of 141b to 1130 (1,1-dichloroethylene) and HF which, in turn, reacts with 141b to produce 142b. It is therefore desirable to find a way to inhibit this breakdown.

In French patent publication no. 2689885, laid open to public inspection on Oct. 15, 1993, (corresponding to U.S. Pat. No. 5,531,867 U.S. patent application Ser. No. 08/119, 905, filed Sep. 10, 1993, which is a continuation of U.S. application Ser. No. 07/983,919, filed Dec. 1, 1992, which is in turn a Continuation-in-Part of U.S. application Ser. No. 07/869,225, filed Apr. 14, 1992) a method is disclosed for improving the Brooks et al. process by inhibiting the formation of 141b, after the photochlorination step, (alone or as a liquid mixture containing 130a or both 130a and 140a) to separate 141b from higher boiling components that may occur in the crude as a result of the photochlorination. This method comprises conducting the heating (a) in the presence of an effective amount of an inhibitor selected from a dialkylhydroxylamine where the alkyl groups have 1 to 4 carbons such as methyl, ethyl, propyl, or butyl [preferably diethylhydroxylamine ("DEHA")]; an epoxide (or cyclic oxide) having 3 to 6 or 10 to 30 carbons such as alpha-pinene oxide ("APO"), 1,2-hexadecene oxide ("HO"), butylene oxide ("BO"), limonene monoxide, limonene dioxide, methyl epoxy soyate, propylene oxide, dicyclopentadiene dioxide alcohol, isoprene oxide, glycidyl isopropyl ether, 1,4-dioxane, or an epoxidized alpha olefin such as $C_{10}H_{20}O$, $C_{12}H24O$, or $C_{16}H_{32}O$ (preferably APO, HO, or BO); a free radical scavenger having at least two double bonds and a boiling point greater than that of 141b such as alpha-methylstyrene ("AMS"), limonene or one of its optical isomers such as d-limonene ("DL"), alloocimene, or isoprene (preferably AMS or DL); a phenol, the phenyl group of which can be unsubstituted or substituted at one or more of the ring positions with substituents separately selected from alkyl (such as methyl, ethyl, isopropyl, butyl), alkoxy (such as methoxy, ethoxy, propoxy, isopropoxy), nitro, halo (such as F, Cl, or Br), alkylamine salt (such as $-N(CH_3)_3{}^+Cl^-$), acyl ($-C(O)R$ where R is alkyl), acyloxy ($-OC(O)R$ where R is alkyl), cyano, hydroxy, phenyl which is unsubstituted or substituted as above, the alkyl portion of such substituents generally being lower alkyl of 1 to 4 carbons, and wherein two adjacent positions of the phenyl group can have substituents which are joined to form a fused aromatic ring as in naphthol (preferred phenols being 2,6-di-t-butyl-4-methylphenol and 4-methoxyphenol); or a 1,4-benzoquinone which can be unsubstituted or substituted at each of the aromatic ring positions with substituents separately selected from those listed for phenol (the preferred benzoquinone being unsubstituted); or (b) in a vessel made of a nickel alloy.

SUMMARY OF THE INVENTION

A method is provided for preventing the conversion of 141b to 142b during the heating of a crude containing mostly 141b to separate 141b from lower boiling components of the crude mixture in a distillation column, either by providing a lining of metal fluoride in the column or by conducting said heating in the presence of an effective amount of a dialkylhydroxylamine an epoxide, a free radical scavenger, a phenol, or a 1,4-benzoquinone inhibitor like that described above with reference to the disclosure of French patent publication no. 26 89 885 and related applications.

This method is particularly applicable to separation of 141b from a liquid mixture containing 142b and, optionally, one or more of 1,1,1-triflouroethane (143a), 1,1-difluoroethane (152a), 1,1,1,3,3-pentafluorobutane (365), 1,1,1-trichloroethane (140a) and 1-chloro-1-fluoroethylene (1131a), in a distillation column. If an inhibitor is used, it is added to the feed of the column in an amount equal to the weight of 141b in the feed. If the column is treated to line it with a coating of metal fluoride, use of an inhibitor is not necessary.

DETAILED DESCRIPTION OF THE INVENTION

In one embodiment of the invention, it has now been found that the presence of the aforementioned inhibitor(s) inhibits the formation of 142b in the 141b bottoms during the heating of 141b, such as occurs when a liquid mixture comprising 141b and 142b is heated in a distillation column to separate low boiling compounds such as 142b from higher boiling compounds, including 141b.

When added to a distillation column, the inhibitor should be added to the crude F141b feed in the feed line to the column. The temperature is highest at the bottom or reboiler section of the column, typically on the order of from about 100° F. to about 250° F. (preferably about 110°–200° F.). The temperature at the top of the column is generally in the range of from about 25 F. to about 155 F. The pressure in the column is generally between 3 and 165 psig. Typically, the column is operated at a pressure of about 70 psig and the temperature is about 202 F. at the bottom and is about 110 F. at the top of the column.

The inhibitor is fed to the column in the F141b crude feed line in an amount of between 100 to 300 ppm, typically 150 to 200 ppm, based on the weight of F141b contained in the feed which will result in an inhibitor concentration in the F141b bottoms of between about 100 to 300 ppm, more typically from between about 150 to about 200 ppm.

This embodiment is illustrated in Examples 1 and 2 below (where percents are weight percent unless otherwise noted). Examples 1 and 2 employ a conventional carbon steel column.

In the alternative embodiment of this invention, it has now been found that the pretreatment of the clean carbon steel column or the vessel in which the heating or distillation is conducted with HF so as to form a film of iron fluoride on the internal surface of the column or vessel is effective to inhibit the formation of 142b without the use of inhibitors. Treatment with a solution of approximately 1.5 wt % HF, preferable in a mixture of 141b and 142b, for about 24 hours followed by purging with inert gas is particularly preferred. Exclusion of air from such processes also assists in the inhibition. This embodiment is illustrated by Example 3.

EXAMPLE 1

(Comparative example)

A crude 141b obtained from the reaction of hydrogen fluoride with 1,1,1-trichloroethane and containing 142b and vinylidene chloride (1130a) and other unsaturated by-products such as 141b, 142b, and 1130a, was distilled in a steam-heated column which was operated at a temperature at the column top of about 110° F., a temperature at the column bottom of about 200° F., and a pressure of about 70 psig. The 141b bottoms typically showed the formation of 1400 to 5300 ppm of 142b.

EXAMPLE 2

Example 1 was repeated except that butylene oxide was added to the F141b crude fed to the column, the amount butylene oxide added to the feed was 150 to 200 ppm based upon the weight of F141b in the feed so that the concentration of butylene oxide in the bottoms was between 150 to 200ppm. The concentration of 142b in the 141b bottoms was reduced to from about 500 to about 1000 ppm, which is within the allowable specification.

EXAMPLE 3

Example 1 was repeated except that before feeding the 141b crude, the (empty) column was exposed to about 1.5 wt. % HF in a mixture of 60% 141b and 142b for about 24 hours, followed by a purge with $N_2$. Distillation as in Example 1 (without addition of BO) resulted in the formation of about 5 to about 200 ppm of 142b.

While the invention has been described herein with reference to specific embodiments, it is not limited thereto. Rather it should be recognized that this invention may be practiced as outline above within the spirit and scope of the appended claims, with such variants and modifications or may be made by those skilled in this art.

What is claimed is:

1. A method for separating 1,1-dichloro-1fluoroethane (141b) from lower boiling components contained in a crude 1,1-dichloro-1-fluoroethane feed stream mixture consisting essentially of the steps of:

selecting a component that will inhibit formation of 1,1-difluoro-1-chloroethane during heating of 1,1-dichloro-1-fluoroethane;

adding said component in the range consisting of from 100 to 300 ppm of said component, based on the weight of 1,1-dichloro-1-fluoroethane in said feed stream mixture, to said feed stream mixture so as to suppress conversion of 1,1-dichloro-1-fluoroethane to 1,1-difluoro-1-chloroethane;

introducing said component and said feed stream mixture into a feed line of a distillation column; and maintaining the temperature of a bottom reboiler section of said column between 100° F. and 250° F. and the pressure between 3 and 165 psig whereby formation of 1,1-difluoro-1-chloroethane is inhibited.

2. A method according to claim 1, wherein the component is butylene oxide.

3. A method according to claim 1 wherein the temperature of between 110° F. and 200° F. is maintained in said bottom reboiler section of said column.

4. A method according to claim 1 wherein said pressure is maintained at about 70 psig.

* * * * *